US012735374B2

(12) United States Patent
Tang et al.

(10) Patent No.: US 12,735,374 B2
(45) Date of Patent: Sep. 15, 2026

(54) PREPARATION METHOD OF TRANS-1,1,1,4,4,4-HEXAFLUORO-2-BUTENE

(71) Applicants: GUANGDONG POWER GRID CO., LTD., Guangzhou (CN); ELECTRIC POWER RESEARCH INSTITUTE OF GUANGDONG POWER GRID CO., LTD., Guangzhou (CN)

(72) Inventors: Nian Tang, Guangzhou (CN); Dongwei Sun, Guangzhou (CN); Zhi Li, Guangzhou (CN); Xiaodian Li, Guangzhou (CN); Li Li, Guangzhou (CN); Manjun Zhang, Guangzhou (CN)

(73) Assignees: GUANGDONG POWER GRID CO., LTD., Guangzhou (CN); ELECTRIC POWER RESEARCH INSTITUTE OF GUANGDONG POWER GRID CO., LTD., Guangzhou (CN)

( * ) Notice: Subject to any disclaimer, the term of this patent is extended or adjusted under 35 U.S.C. 154(b) by 480 days.

(21) Appl. No.: 18/575,384

(22) PCT Filed: Jan. 17, 2023

(86) PCT No.: PCT/CN2023/072716
§ 371 (c)(1),
(2) Date: Dec. 29, 2023

(87) PCT Pub. No.: WO2024/082473
PCT Pub. Date: Apr. 25, 2024

(65) Prior Publication Data

US 2025/0074848 A1 Mar. 6, 2025

(30) Foreign Application Priority Data

Oct. 21, 2022 (CN) ........................ 202211298044.8

(51) Int. Cl.

| | |
|---|---|
| ***C07C 17/35*** | (2006.01) |
| ***B01J 23/02*** | (2006.01) |
| ***B01J 23/58*** | (2006.01) |
| ***B01J 23/89*** | (2006.01) |
| ***B01J 35/30*** | (2024.01) |
| ***B01J 35/61*** | (2024.01) |
| ***B01J 37/00*** | (2006.01) |
| ***B01J 37/02*** | (2006.01) |
| ***B01J 37/08*** | (2006.01) |

(52) U.S. Cl.
CPC ............... *C07C 17/35* (2013.01); *B01J 23/02* (2013.01); *B01J 23/58* (2013.01); *B01J 23/8946* (2013.01); *B01J 35/394* (2024.01); *B01J 35/615* (2024.01); *B01J 37/0018* (2013.01); *B01J 37/0225* (2013.01); *B01J 37/0236* (2013.01); *B01J 37/08* (2013.01)

(58) Field of Classification Search
CPC ......... C07C 17/35; B01J 35/615; B01J 23/58; B01J 23/8946; B01J 37/08
See application file for complete search history.

(56) References Cited

U.S. PATENT DOCUMENTS

2022/0089925 A1 3/2022 Robin et al.

FOREIGN PATENT DOCUMENTS

| | | | |
|---|---|---|---|
| WO | 0107384 | A1 | 2/2001 |
| WO | 2009117458 | A2 | 9/2009 |
| WO | 2015059500 | A1 | 4/2015 |
| WO | 2015142981 | A1 | 9/2015 |
| WO | 2016014348 | A2 | 1/2016 |
| WO | 2016078225 | A1 | 5/2016 |
| WO | 2017027323 | A1 | 2/2017 |
| WO | 2019051389 | A1 | 3/2019 |
| WO | 2019243704 | A1 | 12/2019 |
| WO | 2020150437 | A1 | 7/2020 |
| WO | 2020206335 | A1 | 10/2020 |
| WO | 2021072015 | A1 | 4/2021 |

OTHER PUBLICATIONS

R. N. Haszeldine, The Addition of Free Radicals to Unsaturated Systems, Jan. 1, 1952, pp. 2504-2513.

*Primary Examiner* — Sikarl A Witherspoon

(57) ABSTRACT

The present invention belongs to the technical field of fluorine chemical industry, specifically relates to a preparation method of trans-1,1,1,4,4,4-hexafluoro-2-butene, comprising the following steps: preheating trans-2-ethoxy-1,1,1,4,4,4-hexafluoro-2-butene, mixing with hydrogen, reacting to obtain trans-1,1,1,4,4,4-hexafluoro-2-butene under the action of a catalyst. The selectivity of trans 1,1,1,4,4,4-hexafluoro-2-butene prepared by the preparation method of the present invention can reach 99%, the preparation method adopts moderate reaction temperature and produces less three wastes. The trans 1,1,1,4,4,4-hexafluoro-2-butene prepared by the preparation method has great application value in electric power, electrical appliances and electronics industries.

9 Claims, 3 Drawing Sheets

PREPARATION METHOD OF TRANS-1,1,1,4,4,4-HEXAFLUORO-2-BUTENE

TECHNICAL FIELD

The present invention belongs to the technical field of fluorine chemical industry, specifically relates to a preparation method of trans-1,1,1,4,4,4-hexafluoro-2-butene.

BACKGROUND 1,1,1,4,4,4-hexafluoro-2-butene (HFO-1336mzz) includes cis and trans configurations, where trans (E-HFO-1336mzz) has a boiling point of 7.5° C. and is a colorless, odorless and non-flammable gas at room temperature and under constant pressure. It has environmental-friendly properties (ODP=0, GWP=18, atmospheric life of only 22 days) and high safety. It is non-toxic, flame retardant, oil soluble and has good material compatibility, leading to good application prospect in insulation, heat pump, refrigeration and other fields.

Application in electrical insulation: It has been reported that E-HFO-1336mzz, as a new type of gas developed, has similar excellent properties in electrical insulation and arc extinguishing media, and has a low GWP value, which meets the requirements of environmental protection. According to Siemens, E-HFO-1336mzz has a higher relative dielectric strength than $SF_6$ and can be used as an insulating gas/arc extinguishing medium in electrical installations exceeding 1 kV. The HFO-1336mzz molecule carries six fluorine atoms on the methyl groups at both ends, which can gaseously discharge through dissociative attachment (e.g., the formation of negatively charged fluoride ions) to form a precursor dielectric breakdown. At the same time, compared with other new insulating gases (mainly fluorinated ketones and fluoronitriles), E-HFO-1336mzz has a low atmospheric lifetime and low toxicity.

Application in heat pump working fluid: E-HFO-1336mzz can be used as a heat pump working fluid in high-temperature heat pump and low-temperature heat pump to achieve waste heat recovery, which have high economic value. Jason et al. demonstrated that E-HFO-1336mzz has a higher condensing temperature than working fluids such as HFC-134a, HFO-1234yf, or HFO-1234ze, and its GWP value is at a very low level, while the COPH value is significantly higher, which contributes to its economical use in heat pump applications such as low-pressure steam sterilization, central heating, high-temperature drying, process heating, food manufacturing, drying/dehydration, etc.

The preparation method of E-HFO-1336mzz was reported as early as 1952 (Journal of Chemical Society 1952 2504), in which 2-iodo-hexafluorobutane was synthesized by reacting trifluoroiodomethane with trifluoropropene, and E-HFO-1336mzz was prepared by deiodination under alkaline conditions. In recent years, with the discovery of a variety of excellent properties of E-HFO-1336mzz, more and more relevant patents have been reported, but the existing methods have defects such as poor selectivity to trans products and the need to use chemical quantities of metal elements or bases, such as the method of preparing E-HFO-1336mzz (WO2015142981, WO2009117458) by coupling, using R123 as raw material, requires the use of chemical weight of copper powder as a coupling reagent and the selectivity to trans products is only around 50%. E-HFO-1336mzz can also be prepared by hydrogenation of hexafluorobutyne (WO2017027323, WO2015059500, WO2019243704), because the preparation process needs to be carried out by saponification, the method produces relative more waste alkali, and the cis-selectivity of the product is obviously better than trans. In addition, E-HFO-1336mzz was prepared by R1233xf or R1233zd disclosed in WO2016014348 and WO2001007384, respectively, and the reaction temperature reached 600-725° C. due to the high-temperature pyrolysis process adopted, which was very energy-intensive. Fluorination is also one of the important methods for the preparation of E-HFO-1336mzz, which uses polyhaloalkanes and anhydrous hydrogen fluoride under the action of catalysts, but the cis- and anti-selectivity of the product is more dependent on temperature (WO2015142981, WO2016078225, WO2020206335, WO2019051389).

SUMMARY

In view of the deficiencies and defects existing in the prior work, the invention aims to provide a preparation method of trans-1,1,1,4,4,4-hexafluoro-2-butene. The selectivity to trans-1,1,1,4,4,4-hexafluoro-2-butene achieved by this preparation method can reach 99%, and the preparation method adopts a moderate reaction temperature and produces less wastes (waste gas, waste water and industrial residue). The trans-1,1,1,4,4,4-hexafluoro-2-butene prepared by this preparation method has great application value in electric power, electrical and electronic industries.

In order to achieve the above purpose, the invention adopts the following technical solution: a preparation method of trans-1,1,1,4,4,4-hexafluoro-2-butene, comprising the following steps:

preheating trans-2-ethoxy-1,1,1,4,4,4-hexafluoro-2-butene, then mixing with hydrogen, and reacting in the presence of a catalyst to obtain trans-1,1,1,4,4,4-hexafluoro-2-butene;

the catalyst includes an aluminum-magnesium composite oxide and a group VIII transition metal.

Preferably, the aluminum-magnesium composite oxide has a molecular sieve-like structure and a microporous structure.

Preferably, a molar ratio of 2-ethoxy-1,1,1,4,4,4-hexafluoro-2-butene to the hydrogen is 1:(1-5). More preferably, the molar ratio of 2-ethoxy-1,1,1,4,4,4-hexafluoro-2-butene to the hydrogen is 1:(2-4).

Preferably, the aluminum-magnesium composite oxide has a BET surface area of 200-500 $m^2/g$.

Preferably, the group VIII transition metal is one or two selected from the group consisting of Ru, Ni and Co.

Preferably, the group VIII transition metal has a mass content of 0.5~10.0 wt % of the total mass of the catalyst.

Preferably, a preparation method of the aluminum-magnesium composite oxide comprises the following steps:

taking an aluminum-containing compound and a magnesium-containing compound as raw materials, adding polyethylene glycol or an organic amine as a stencil, and synthesizing the aluminum-magnesium composite oxide by hydrothermal method, solvothermal method or dry gel conversion method. Described hydrothermal method, solvothermal method and dry gel conversion method are all conventional technologies in the art.

Preferably, the preparation method of trans-1,1,1,4,4,4-hexafluoro-2-butene comprises at least one of the following (1)-(2):

(1) the aluminum-containing compound includes at least one selected from the group consisting of aluminum hydroxide, pseudo-boehmite, hydrated alumina, and aluminum isopropanol;

(2) the magnesium-containing compound includes at least one selected from the group consisting of magnesium oxide, magnesium nitrate, magnesium acetate and magnesium metal.

Preferably, the preparation method of the catalyst comprises the following steps:

immersing the aluminum-magnesium composite oxide in a group VIII transition metal solution, drying, and calcinating at a constant temperature of 500-600° C. in a muffle furnace to obtain the catalyst.

Preferably, the preparation method of trans-1,1,1,4,4,4-hexafluoro-2-butene comprises at least one of the following (1)-(3):

(1) the reacting is carried out at a temperature of 150-250° C.;

(2) the reacting is carried out at a space velocity of 1.0-5.0 $h^{-1}$;

(3) the reacting is carried out under a pressure of 0.2-2.0 MPa.

More preferably, the preparation method of trans-1,1,1,4,4,4-hexafluoro-2-butene comprises at least one of the following (1)-(3):

(1) the reacting is carried out at a temperature of 180-225° C.;

(2) the reacting is carried out at a space velocity of 1.5-2.5 $h^{-1}$;

(3) the reacting is carried out under a pressure of 0.4-1.0 MPa.

Compared with the prior art, the present invention has the following beneficial effects:

In the present invention, trans-1,1,1,4,4,4-hexafluoro-2-butene is prepared by a one-step process in a fixed-bed reactor, adopting a supported catalyst. The reaction temperature of the process is moderate, and trans selectivity of the product is high (up to 99%). 2-ethoxy-1,1,1,4,4,4-Hexafluoro-2-butene is used as raw material in the present invention, which can not only make the active ingredients of the catalyst more oxyphilic, but also improves the catalytic activity of the catalyst since the alkoxy group removed by the catalyst during the reaction process will not cause catalyst poisoning.

DETAILED DESCRIPTION OF THE EXAMPLES

The following will provide a clear and complete description of the technical solutions in the embodiments of the present invention, in conjunction with the embodiments of the present invention. Obviously, the described embodiments are only a part of the embodiments of the present invention, not all of them. Based on the embodiments in the present invention, all other embodiments obtained by ordinary skilled in the art without creative labor fall within the protection scope of the present invention.

In the embodiments and comparison examples, unless otherwise specified, the experimental methods used are conventional methods. The materials, reagents, etc. used can be obtained from commercial sources.

Example 1: Preparation Method of trans 1,1,1,4,4,4-hexafluoro-2-butene (1) Preparation of Carrier Pseudo-boehmite and magnesium oxide were mixed in a weight ratio of 45:55, and dissolved in dilute nitric acid. Template agent polyethylene glycol 10000 was added, and a resulting mixture was dried at 100° C., and then calcinated in a muffle furnace at 500° C. for 8 hours, to obtain a catalyst carrier;

(2) Preparation of Catalyst

The catalyst carrier was immersed in a mixed solution of 5 g/1000 mL ruthenium nitrate and 5 g/1000 mL nickel nitrate, with a solid-liquid ratio of 1:1. A resulting product was dried at 100° C., and then calcinated at a constant temperature of 500° C. in a muffle furnace for 6 hours, to obtain a finished product of 0.5% catalyst, denoted as $0.5Ru/0.5Ni/Al_xMg_yO_z$;

(3) Effect Evaluation of the Catalyst

The evaluation was conducted in a continuous fixed bed reactor. 10 ml of the catalyst was loaded, hydrogen was used as a carrier gas and 2-ethoxy-1,1,4,4,4-hexafluoro-2-butene was a reactant. The reactant is fed by a liquid micro pump. The molar ratio of 2-ethoxy-1,1,4,4,4-hexafluoro-2-butene to hydrogen was 1:2, the space velocity was controlled at 2.5 $h^{-1}$, the reaction pressure was 1.0 MPa, and the reaction temperature was 225° C. After 6 hours of reaction, sample of the gas phase composition in the reactor was analyzed by gas chromatography. The conversion rate was 97% and the selectivity was 99%.

Figure 1:
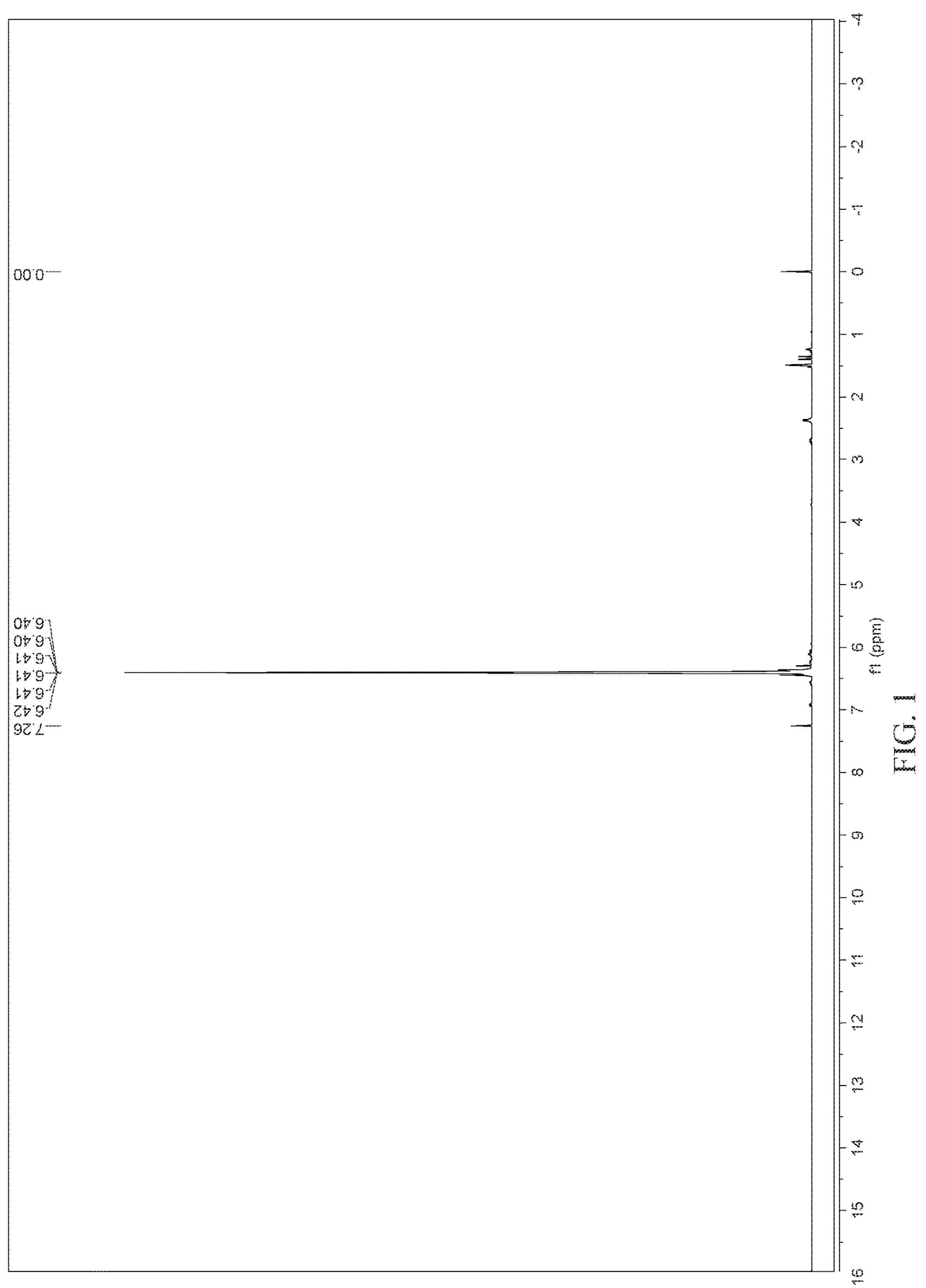
FIG. 1 shows the hydrogen spectrum of trans 1,1,1,4,4,4-hexafluoro-2-butene prepared in Example 1 of the present invention.
Figure 2:
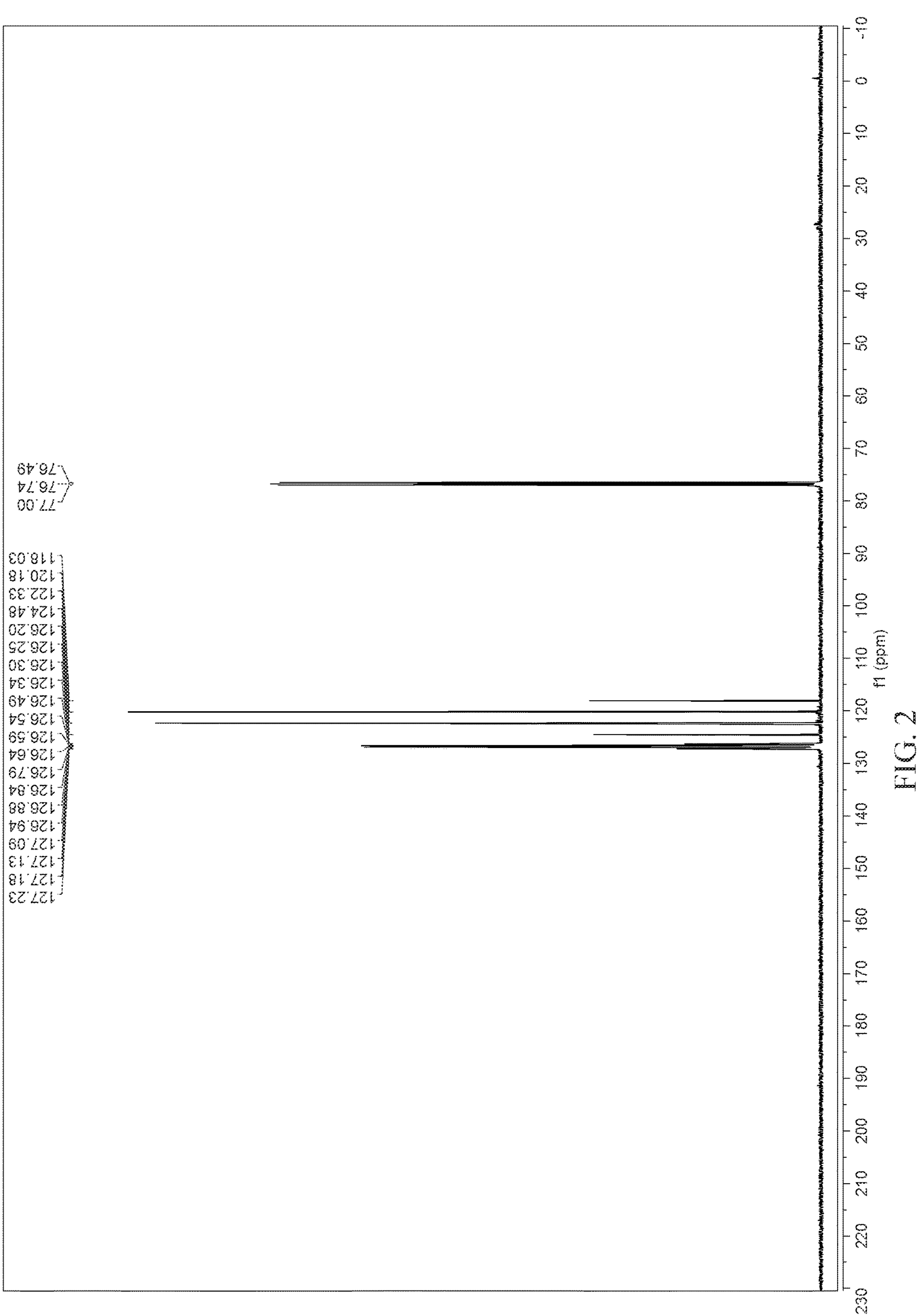
FIG. 2 shows the carbon spectrum of trans-1,1,1,4,4,4,4-hexafluoro-2-butene prepared in Example 1 of the present invention.
Figure 3:
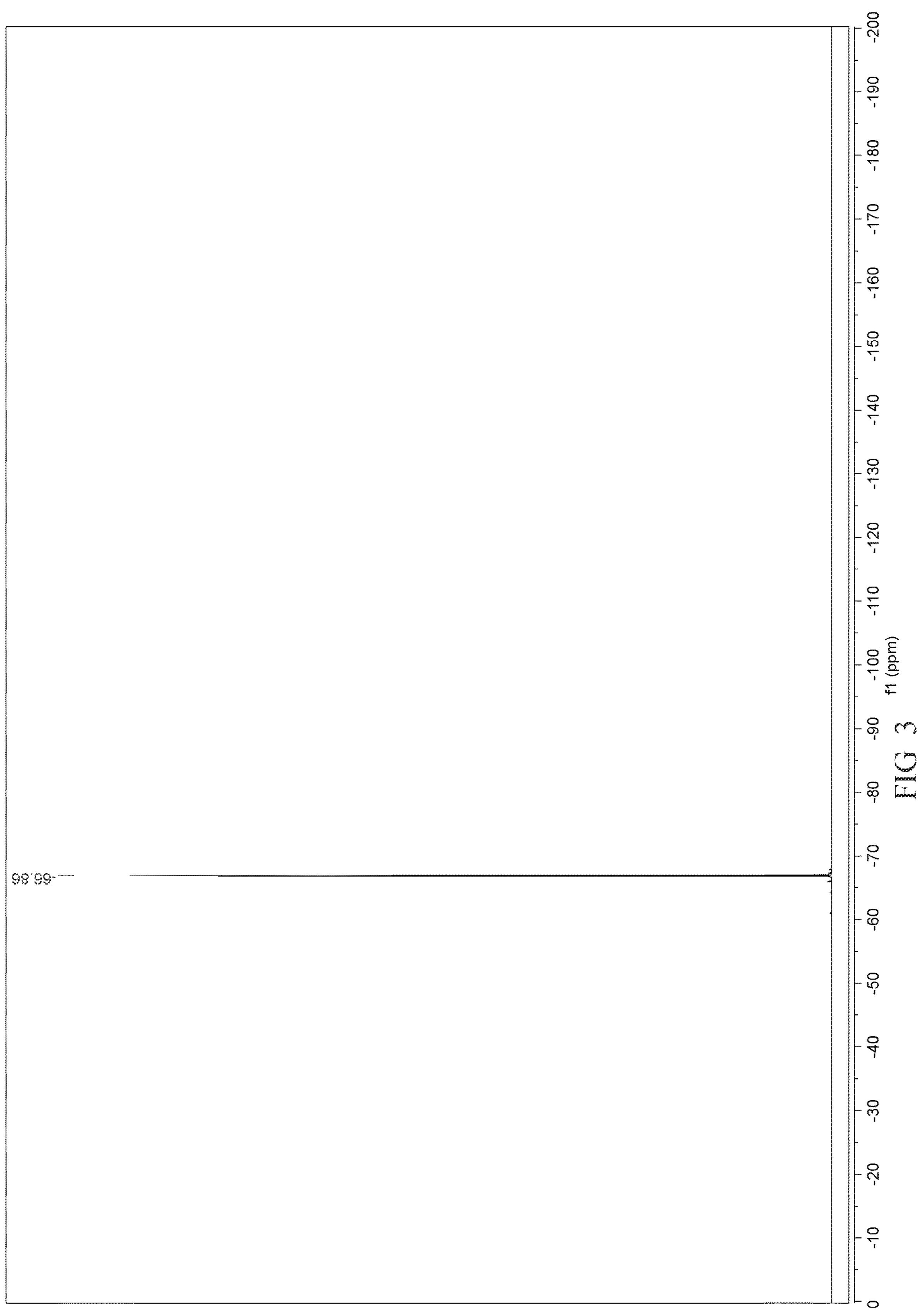
FIG. 3 shows the fluorine spectrum of trans-1,1,1,4,4,4,4-hexafluoro-2-butene prepared in Example 1 of the present invention.

The nuclear magnetic resonance data of the reaction product are shown in FIGS. 1-3.

Examples 2-4

Examples 2-4 were conducted based on Example 1, except that the reaction temperatures were different.

The specific parameters, conversion rate, and selectivity results are shown in Table 1.

TABLE 1

| Examples | Reaction temperature/° C. | Conversion rate (%) | Selectivity (%) |
|---|---|---|---|
| 2 | 150 | 80 | 88 |
| 3 | 180 | 93 | 97 |
| 4 | 250 | 97 | 63 |

Examples 5-7

Examples 5-7 were conducted based on Example 1, except that the reaction pressures were different.

The specific parameters, conversion rate, and selectivity results are shown in Table 2.

TABLE 2

| Examples | Reaction pressure/MPa | Conversion rate ( %) | Selectivity (%) |
|---|---|---|---|
| 5 | 0.2 | 79 | 83 |
| 6 | 0.4 | 84 | 95 |
| 7 | 2.0 | 95 | 81 |

Examples 8-10

Examples 8-10 were conducted based on Example 1, except that the space velocity was changed to evaluate its effect on the reaction.

The specific parameters, conversion rate, and selectivity results are shown in Table 3.

TABLE 3

| Examples | Space velocity/$h^{-1}$ | Conversion rate (%) | Selectivity (% ) |
|---|---|---|---|
| 8 | 1.0 | 75 | 82 |
| 9 | 1.5 | 95 | 95 |
| 10 | 5.0 | 82 | 64 |

Examples 11-13

Examples 11-13 were conducted based on Example 1, except that the molar ratio of 2-ethoxy-1,1,4,4,4-hexafluoro-2-butene to hydrogen gas was changed to evaluate its effect on the reaction.

The specific parameters, conversion rate, and selectivity results are shown in Table 4.

TABLE 4

| Examples | the molar ratio of 2-ethoxy-1,1,4,4,4-hexafluoro-2-butene to hydrogen gas | Conversion rate ( %) | Selectivity (%) |
|---|---|---|---|
| 11 | 1:1 | 78 | 79 |
| 12 | 1:4 | 95 | 96 |
| 13 | 1:5 | 89 | 88 |

Examples 14-20

Examples 14-20 were conducted based on Example 1, except that the catalyst composition and the mass content of the group VIII transition metal were changed to evaluate their effects on the reaction.

The specific parameters, conversion rate, and selectivity results are shown in Table 5.

TABLE 5

| Examples | Catalyst composition | Conversion rate (%) | Selectivity (%) |
|---|---|---|---|
| 14 | $0.5Ru/Al_xMg_yO_z$ | 73 | 75 |
| 15 | $2.0Ru/Al_xMg_yO_z$ | 88 | 91 |
| 16 | $5.0Ru/Al_xMg_yO_z$ | 92 | 90 |
| 17 | $5.0Ru/2.5Ni/Al_xMg_yO_z$ | 91 | 93 |
| 18 | $5.0Ru/5.0Ni/Al_xMg_yO_z$ | 93 | 97 |
| 19 | $5.0Ru/2.5Co/Al_xMg_yO_z$ | 78 | 98 |
| 20 | $5.0Ru/5.0Co/Al_xMg_yO_z$ | 89 | 99 |

Comparative Example 1

The present comparative example was conducted based on Example 1, except that the reaction temperature was 100° C.

The conversion rate was 32% and the selectivity was 78%.

Comparative Example 2

The present comparative example was conducted based on Example 1, except that the reaction pressure was 2.5 MPa.

The conversion rate was 80% and the selectivity was 35%.

Comparative Example 3

The present comparative example was conducted based on Example 1, except that the space velocity was 0.5 $h^{-1}$.

The conversion rate was 72% and the selectivity was 54%.

Comparative Example 4-5

The present comparative example was conducted based on Example 1, except that the molar ratios of 2-ethoxy-1,1,4,4,4-hexafluoro-2-butene to hydrogen gas were different.

The specific parameters, conversion rate, and selectivity results are shown in Table 6.

TABLE 6

| Comparative examples | the molar ratio of 2-ethoxy-1,1,4,4,4-hexafluoro-2-butene to hydrogen gas | Conversion rate (%) | Selectivity (%) |
|---|---|---|---|
| 4 | 1:10 | 25 | 47 |
| 5 | 1:0.5 | 38 | 26 |

Comparative Examples 6-8

The comparative examples 6-8 were conducted based on Example 1, except that the catalyst compositions were different.

The specific parameters, conversion rate, and selectivity results are shown in Table 7.

TABLE 7

| Comparative examples | Catalyst composition | Conversion rate (%) | Selectivity (%) |
|---|---|---|---|
| 6 | 0.5Pd/0.5Cu/AlxMgyOz | 15 | 48 |
| 7 | 0.5Pt/0.5La/AlxMgyOz | 39 | 76 |
| 8 | 0.5Ru/0.5Ni/AlxMgyOz | 32 | 85 |

Comparative Examples 9-10

The comparative examples 9-10 were conducted based on Example 1, except that the raw material compositions were different.

The specific parameters, conversion rate, and selectivity results are shown in Table 8.

TABLE 8

| Comparative examples | Raw material composition | Conversion rate (%) | Selectivity (%) |
|---|---|---|---|
| 9 | $CF_3CH{=}CClCF_3$ | 21 | 33 |
| 10 | $CF_3CH{=}CFCF_3$ | 29 | 42 |

The above embodiments are only illustrative of the principle and technical effect of the present invention, and are not intended to limit the invention. Any skilled in the arts may modify or change the above embodiments without departing from the spirit and scope of the present invention. Therefore, all equivalent modifications or changes within the spirit and technical ideas disclosed in the present invention and completed by those with ordinary knowledge in the technical field should still be covered by the claims of the present invention.

The invention claimed is:

1. A preparation method of trans-1,1,1,4,4,4-hexafluoro-2-butene, comprising the following steps:

preheating trans-2-ethoxy-1,1,1,4,4,4-hexafluoro-2-butene, then mixing it with hydrogen, and reacting in the presence of a catalyst to obtain trans-1,1,1,4,4,4-hexafluoro-2-butene;

the catalyst comprises an aluminum-magnesium composite oxide and a group VIII transition metal.

2. The preparation method of trans-1,1,1,4,4,4-hexafluoro-2-butene according to claim 1, wherein a molar ratio of the trans-2-ethoxy-1,1,1,4,4,4-hexafluoro-2-butene to the hydrogen is 1:(1-5).

3. The preparation method of trans-1,1,1,4,4,4-hexafluoro-2-butene according to claim 1, wherein the aluminum-magnesium composite oxide has a BET surface area of 200-500 m2/g.

4. The preparation method of trans-1,1,1,4,4,4-hexafluoro-2-butene according to claim 1, wherein the group VIII transition metal is one or two selected from the group consisting of Ru, Ni and Co.

5. The preparation method of trans-1,1,1,4,4,4-hexafluoro-2-butene according to claim 1, wherein the group VIII transition metal has a mass content of 0.5-10.0 wt % of a total mass of the catalyst.

6. The preparation method of trans-1,1,1,4,4,4-hexafluoro-2-butene according to claim 1, wherein the aluminum-magnesium composite oxide is prepared by the following steps:

taking an aluminum-containing compound and a magnesium-containing compound as raw materials, adding polyethylene glycol or an organic amine as a stencil, and synthesizing the aluminum-magnesium composite oxide by hydrothermal, solvothermal or dry gel conversion methods.

7. The preparation method of trans-1,1,1,4,4,4-hexafluoro-2-butene according to claim 6, comprising at least one of the following (1)-(2):

(1) the aluminum-containing compound comprises at least one selected from the group consisting of aluminum hydroxide, pseudo-boehmite, hydrated alumina, and aluminum isopropanol;

(2) the magnesium-containing compound comprises at least one selected from the group consisting of magnesium oxide, magnesium nitrate, magnesium acetate and magnesium metal.

8. The preparation method of trans-1,1,1,4,4,4-hexafluoro-2-butene according to claim 1, comprising at least one of the following (1)-(3):

(1) the reacting is carried out at a temperature of 150-250° C.;

(2) the reacting is carried out at a space velocity of 1.0-5.0 $h^{-1}$;

(3) the reacting is carried out under a pressure of 0.2-2.0 MPa.

9. The preparation method of trans-1,1,1,4,4,4-hexafluoro-2-butene according to claim 8, comprising at least one of the following (1)-(3):

(1) the reacting is carried out at a temperature of 180-225° C.;

(2) the reacting is carried out at a space velocity of 1.5-2.5 $h^{-1}$;

(3) the reacting is carried out under a pressure of 0.4-1.0 MPa.

* * * * *